(12) United States Patent
Wong

(10) Patent No.: US 8,866,085 B1
(45) Date of Patent: Oct. 21, 2014

(54) DIFFERENTIAL TEMPERATURE SOURCE NDIR GAS SENSING METHODOLOGY

(71) Applicant: Airware, Inc., Goleta, CA (US)

(72) Inventor: Jacob Y Wong, Goleta, CA (US)

(73) Assignee: Airware, Inc, Goleta, CA (US)

( * ) Notice: Subject to any disclaimer, the term of this patent is extended or adjusted under 35 U.S.C. 154(b) by 137 days.

(21) Appl. No.: 13/674,473

(22) Filed: Nov. 12, 2012

(51) Int. Cl.
*G01N 21/3581* (2014.01)
*G01N 21/3504* (2014.01)

(52) U.S. Cl.
USPC ................................ 250/343; 250/341.1

(58) Field of Classification Search
CPC .................. G01N 21/3504; G01N 21/274
USPC ............................... 250/343, 341.1
See application file for complete search history.

(56) References Cited

U.S. PATENT DOCUMENTS 5,026,992 A * 6/1991 Wong ........................ 250/343

OTHER PUBLICATIONS

"Zero drift NDIR gas sensors" Sensor Review, Emerald Group Publishing, vol. 31, issue 1 (2011), to Wong et al.*

* cited by examiner

*Primary Examiner* — David Porta
*Assistant Examiner* — Kenneth J Malkowski
(74) *Attorney, Agent, or Firm* — Roy L. Anderson; Wagner Anderson & Bright PC

(57) ABSTRACT

A differential temperature source methodology for the design of a single beam NDIR gas sensor is advanced. This methodology uses a low and a high amplitude voltage cycle to drive a closely approximated Blackbody source for generating at different times two distinct detector outputs obtained from the same detector equipped the same narrow band pass filter but strategically designed for the detection of only a particular portion of the absorption band for the gas of interest. The ratio of the high amplitude cycle detector output over the low amplitude cycle detector output is used to calibrate such an NDIR gas sensor after it is normalized by a similar ratio when there is no target gas present in the sample chamber.

2 Claims, 8 Drawing Sheets

# DIFFERENTIAL TEMPERATURE SOURCE NDIR GAS SENSING METHODOLOGY

FIELD OF THE INVENTION

The present invention is in the field of non-dispersive infrared (NDIR) gas sensors of a type used to measure the concentrations of unwanted or combustible gases so that an alarm can be enunciated when their concentration approaches or exceeds a harmful or dangerous level. More specifically, the present invention relates to a comparatively small, simple and low cost apparatus having no moving parts and capable of measuring the concentration of most common gases in the atmosphere.

BACKGROUND OF THE INVENTION

The NDIR technique utilizing the characteristic absorption bands of gases in the infrared has been widely used for decades in the gas analyzer industry for the detection of these gases. Such gas analyzers utilize the principle that various gases exhibit substantial absorption at specific wavelengths in the infrared radiation spectrum. The term "non-dispersive" as used herein refers to the apparatus used, typically a narrow-band optical or infrared transmission filter instead of a dispersive element such as a prism or diffraction grating, for isolating for the purpose of measurement the radiation in a particular wavelength band that coincides with a strong absorption band of a gas to be measured. The NDIR technique has long been considered as one of the best methods for gas measurement. In addition to being highly specific, NDIR gas sensors are also very sensitive, relatively stable and easy to operate and maintain. In contrast to NDIR gas sensors, the majority of other types of gas sensors today are in principle interactive. Interactive gas sensors are less reliable, short-lived and generally nonspecific, and in some cases can be poisoned or saturated into a nonfunctional or irrecoverable state.

Despite the fact that interactive gas sensors are mostly unreliable and that the NDIR gas measurement technique is one of the best there is NDIR gas sensors still have not enjoyed widespread high volume usage to date. There are three main reasons for this. First, there are several applications in existence today that would require a very large number of gas sensors typically running into millions of units per annum. One very prominent example of these is the long overdue smart fire detector that needs the assistance of gas sensors for detecting specific effluent gases from a fire such as Carbon Monoxide and Carbon Dioxide. Detection of these effluent gases when a fire first breaks out would greatly help the conventional smoke detector not only to eliminate most of its nuisance false alarms but also to detect fires like smoldering or even fast-moving ones in a much shorter time. But gas sensors to be deployed in such an application must be extraordinarily reliable and just about all gas sensors ever designed and manufactured to date, irrespective of what technology is being employed, invariably have significant output drifts over time.

Another high volume usage example in the millions of units per annum range is the so-called "harmful or dangerous gas level fuse." Many gas heaters, inclusive of kerosene heaters and gas water heaters, are required by law to have a safety device equipped with the heater in order to warn users of poor ventilation and hence low oxygen levels in the heater's enclosed space. Either an NDIR high Carbon Dioxide fuse (for detecting CO2 levels>5,000 ppm) or an NDIR high Hydrocarbon fuse (for detecting lower explosion limit [LEL] >2.5%) would be a much better candidate for use than an expensive, short lifespan and unreliable electrochemical oxygen sensor. However, such NDIR gas level fuses must once again be extraordinarily reliable and should not require frequent re-calibration in order to assure their output accuracy over time.

The second reason why today's NDIR gas sensors do not enjoy widespread high volume usage has to do with their size. They are typically several inches in length, width and height dimensions. Like in the application cases mentioned above with regard to their potential use as an augmented smart smoke detector or as a "harmful or dangerous gas level fuse," their sizes are generally considered to be too big. Even if they have overcome their output drift reliability problem, their physical dimensions remain a significant impediment to their utilization and must be drastically reduced to gain usefulness. Although the size of NDIR gas sensors has indeed been greatly reduced to just a couple of inches in all three dimensions during the past couple of years, they still have to be further reduced, preferably to just thumb-sized scales, in order to remove their size hindrance in a number of high volume usage applications.

Recently the present author in issued U.S. Pat. No. 8,003, 944 ("Saturation filtering NDIR gas sensing methodology"), Aug. 23, 2011, U.S. Pat. No. 8,143,581 ("Absorption biased NDIR gas sensing methodology"), Mar. 27, 2012 and U.S. Pat. No. 8,217,355 ("Self-commissioning NDIR gas sensors"), Jul. 10, 2012 disclosed teachings which are capable of eliminating substantially all NDIR gas sensor output drifts over time. These methodologies represent for the first time an NDIR gas sensor that can now be designed and manufactured to overcome this performance deficiency. Furthermore, these methodologies, when appropriately implemented, are capable of reducing the size of NDIR gas sensors to thumb-sized dimensions thereby removing for the first time any size hindrances affronting them in many high volume usage applications.

The third reason why NDIR gas sensors do not enjoy widespread high volume usages is their unit sensor cost which has been too high for almost all such applications. Recalling about four decades ago, an NDIR medical CO2 sensor was sold for more than $10,000.00 each. By the early 1990's, the unit price for an NDIR CO2 sensor dropped to less than $500.00. Today the unit price of an NDIR CO2 sensor goes for about $200.00, reflecting the fact that the unit production cost for such a sensor has to be just around $50.00 or less. But even this unit production cost today is considered to be too high for many applications including the two examples mentioned above, namely the augmented smart smoke detector and the "harmful or dangerous gas level fuse". For both of these applications, the unit production cost for an NDIR gas sensor has to be well under $10.00.

Since the first two out of three main reasons why NDIR gas sensors do not enjoy widespread high volume usages today appear to be under control for elimination as noted above, the object of the present invention is to reduce the unit production cost for NDIR gas sensors to an absolute minimum possibly just a few dollars. This unit production cost is likely to be the ultimate bottom price for future non-interactive NDIR gas sensors. As it turns out, when comparing the difficulty to overcome this third reason as versus overcoming the first two, it is indeed the toughest.

The current invention reduces unit cost by reducing component cost while at the same time rendering the implemented NDIR gas sensor with significantly reduced output drifts over time and also with thumb-sized dimensions. As a result, the current invention not only eliminates the first two reasons why NDIR gas sensors have not enjoyed to date widespread usages as discussed above, but also allows an NDIR gas sensor to be designed and manufactured for the first time with volume unit production cost well under $10.00.

SUMMARY OF THE INVENTION

The present invention is generally directed to a single beam NDIR gas sensor and process for using it in which infrared radiation is emitted from a single infrared source into a sample chamber that is alternatively pulsed at a high temperature and at a low temperature, the infrared radiation is detected after it passes through a narrow band pass filter with a spectral characteristic that substantially overlaps a strong absorption band for the gas to be detected, and the concentration of the gas is determined by use of an absorption bias between a signal output of the detector at the high temperature and a reference output of the detector at the low temperature, the convoluted output of the single infrared source and the narrow band pass filter being substantially coincident with the strong absorption band.

It is therefore a primary object of the present invention to advance an improved single-beam NDIR gas sensor and methods of using it.

This and further objects and advantages will be apparent to those skilled in the art in connection with the drawings and the detailed description of the invention set forth below.

DETAILED DESCRIPTION OF THE INVENTION

Figure 1:
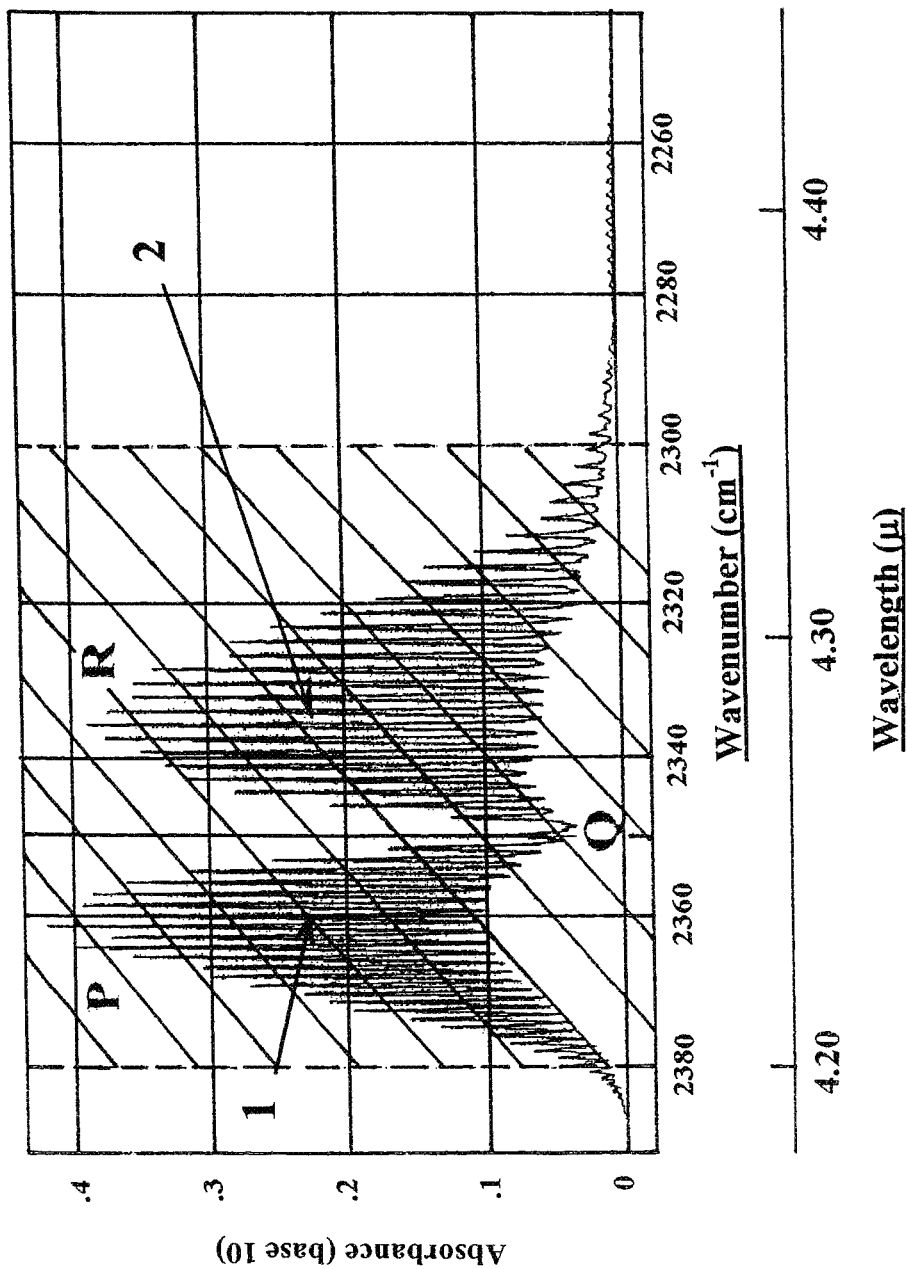
FIG. 1. The infrared absorption band of $CO_2$ gas at 4.259μ.

In order to improve the performance and cost of the ever popular dual beam NDIR gas sensor, one has to seek favorable opportunities in the gas sensor assembly end of this class of devices. Needless to say, if one can reduce the number of detectors from two to one, including the narrow band pass transmission filter that normally comes with them, which in effect reduces the dual beam configuration into a single beam one, while at the same time rendering this new and simplified technique adequately workable for an accurate, reliable and stable NDIR gas sensor, then the goal of achieving an ultra low cost NDIR gas sensor might be accomplished. The use of only one infrared source and one detector to configure an NDIR gas sensor is commonly known as the Single Beam methodology and was in fact the first one deployed almost six decades ago. Although a single beam implementation for an NDIR gas sensor is absolutely the simplest methodology possible, over the years people soon found out that it has numerous drawbacks, including severe sensor output drifts, output changes due to optics contamination and external temperature dependences.

The first task at hand therefore is to find out how to create spectrally and functionally a dual beam equivalent performance situation with only a single infrared source and a single detector. One conclusion that one can draw rather quickly is that since the roles played by the detectors are quite rigid, reducing the number of them from two to one would seem to be almost impossible. The only remaining approach would be to try to do something with the infrared source which is more dynamic or flexible. As disclosed earlier in U.S. Pat. No. 5,026,992 (1991) by the present author, the disclosure of which is specifically incorporated herein by reference, one can change the spectral characteristic output of a blackbody source according to Planck's radiation curves by driving it at different power levels in order to reach different operating blackbody temperatures. This can be readily achieved since one has to pulse the infrared source anyway as in the case for the dual beam gas sensing technique. By so doing it is possible to create two beams at different times with different spectral output characteristics for the source.

The present invention takes advantage of the fact that one can create both a Reference channel and a Signal channel by using the technique of a differential temperature source with just one infrared source and one detector or the so-called Single Beam methodology approach. This is accomplished by the use of a low amplitude source drive cycle as the Reference channel when the source temperature is rendered very low followed by a high amplitude source drive cycle as the Signal channel when the source temperature is rendered relatively high.

Following the teaching for the design of an output stable dual beam NDIR gas sensor as disclosed in U.S. Pat. No. 8,143,581 by Wong (2012) where an absorption bias was created between the Reference channel and the Signal channel in order to afford sensor calibration for the gas of interest, if a similar absorption bias can be created for the current Single Beam approach between the Reference channel (low amplitude source drive) and the Signal channel (high amplitude source drive), then the sensor output for the currently invented Single Beam methodology will also be stable over time. For the methodology to work as exemplified in U.S. Pat. No. 8,143,581, the disclosure of which is specifically incorporated herein by reference, both the Reference channel detector and the Signal channel detector must have narrow band pass filters with the same spectral characteristics, namely the same CWL and FWHM. Because of this, the ratio for the Signal channel detector output over the Reference channel detector output will not be affected by the spectral changes of the source due to aging over time. In the currently invented differential temperature source Single Beam methodology, this condition is satisfied because both the Reference channel and the Signal channel share the same detector having the same filter but are operated at different times.

The current invention discloses a novel and critical sensor component design feature that is necessary for creating the needed absorption bias between the Reference channel (low amplitude drive cycle) and the Signal channel (high amplitude drive cycle) for the differential temperature source Single Beam sensor design approach in order to achieve stable output performance. This novel design feature is a strategic design for the narrow band pass filter installed and located in front of the infrared detector. In order to illustrate more clearly this novel design feature, we shall use an NDIR CO2 sensor as an example, although the present invention is not limited solely to detection of CO2 gas.

Figure 2:
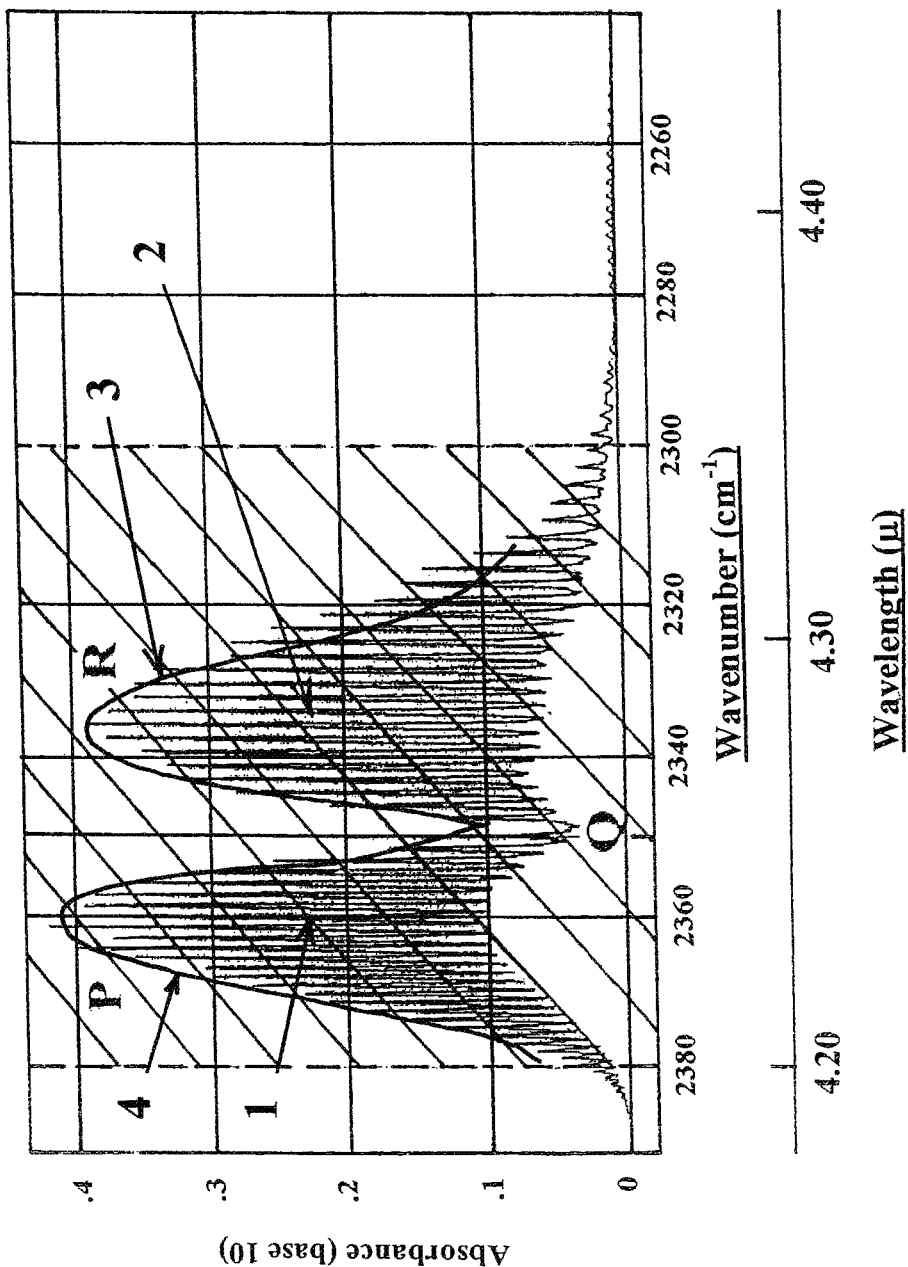
FIG. 2. Novel narrow band pass filter designs for the current invention.

FIG. 1 shows the infrared absorption band of CO2 gas at 4.259µ showing respectively, 1 and 2, the P and R branches of sharp absorption lines. The current novel component design feature dictates that the spectral characteristic for this filter should substantially overlap the R branch absorption lines of CO2 gas as shown by filter 3 in FIG. 2, which means the spectral characteristic for this filter should closely overlap the R branch absorption lines. As depicted in FIG. 2, this filter 1 will have a CWL=4.285µ and a FWHM=0.049µ. The transmittance of the filter at CWL is not critical but should be better than 0.7. Alternatively, the current novel design feature can also dictate that the spectral characteristic for this filter has to overlap as closely as possible the P branch absorption lines of the CO2 gas as shown by filter 4 in FIG. 2 with CWL=4.237µ and FWHM=0.031µ. For clarity of discussion, we shall focus only on the use of filter 3 in FIG. 2 to describe details regarding the current invention. With the design for the spectral characteristics of this filter 3 specified above, it is now possible to adjust the voltage levels for both the low and the high amplitude drive cycles respectively for the Reference and the Signal channels in order to create an absorption bias between the channels for the gas of interest (in the current example CO2) as will be explained in more detail below.

Figure 3:
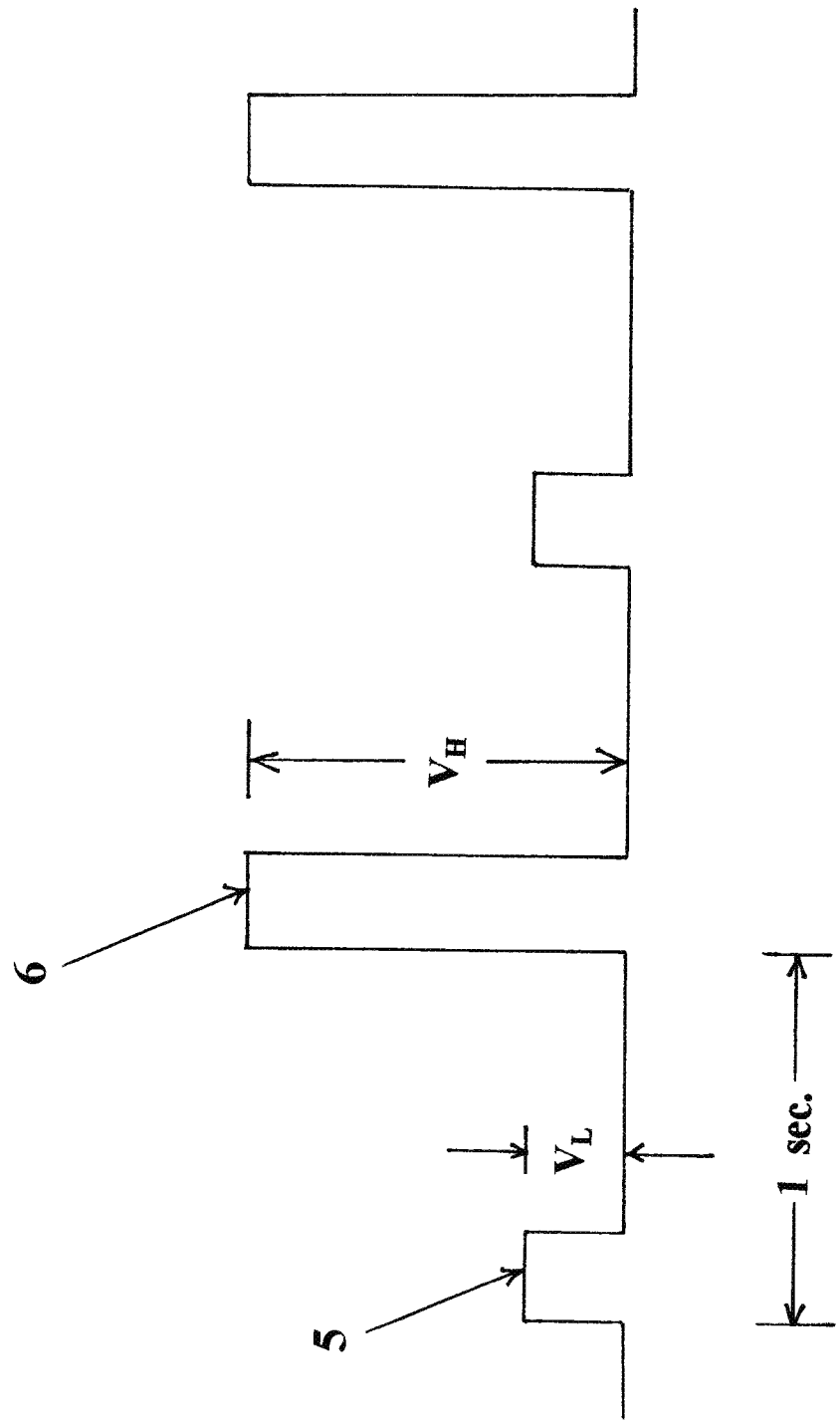
FIG. 3. Low and high amplitude voltage cycles for driving the source in the current invention.
Figure 4:
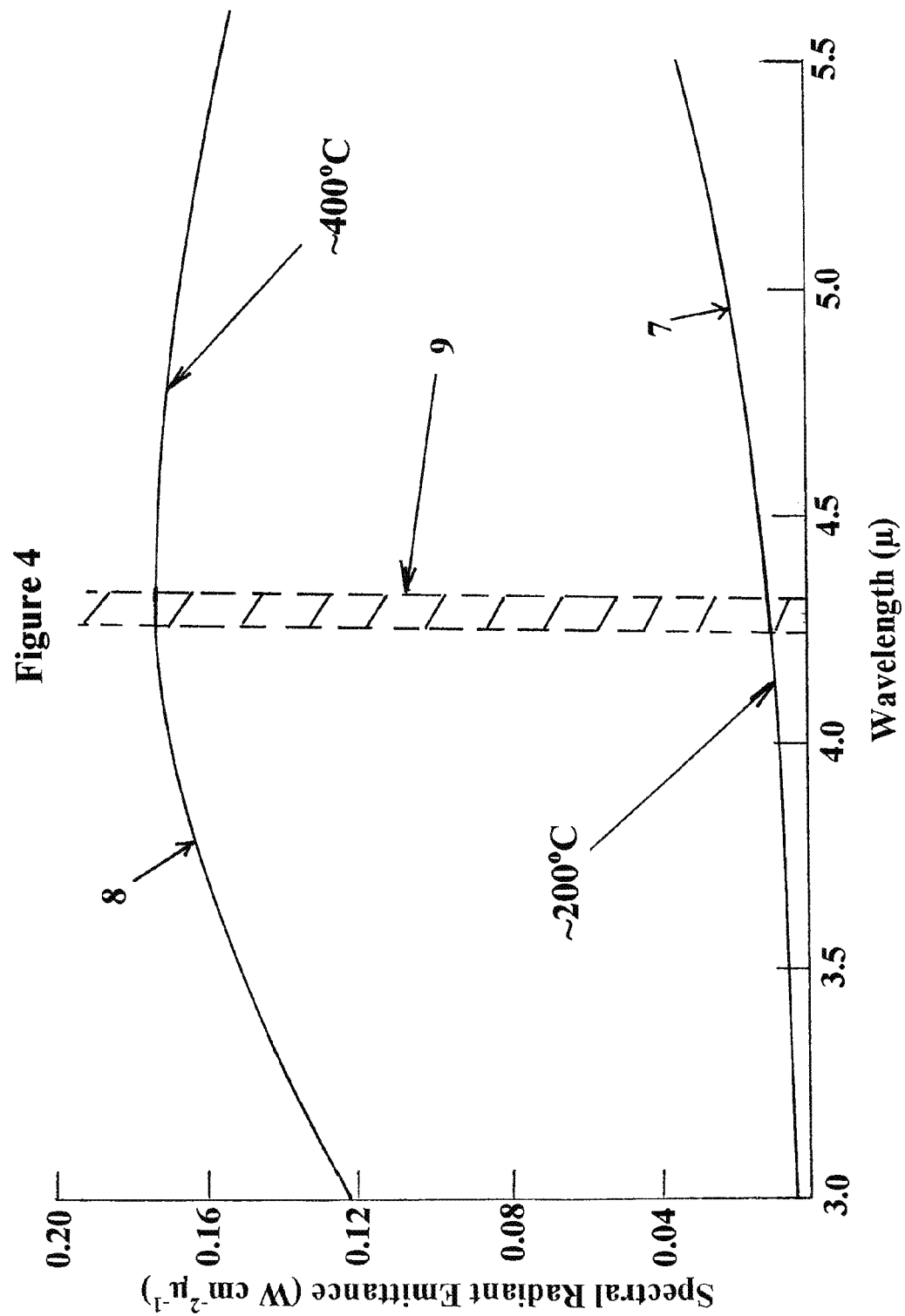
FIG. 4. Spectral radiant emittance for the low (~200° C.) and high (~400° C.) amplitude drive for the source.

The differential temperature source technique is achieved via creating a low amplitude drive cycle and a high amplitude drive cycle for the source alternately in time. During the low amplitude cycle, the driving voltage for the source is kept low and during the high amplitude cycle the driving voltage is kept relatively high. FIG. 3 shows a typical voltage waveform (typical frequency of 1 Hz and 20% duty factor) for driving the source of the sensor in the current invention. With reference to FIG. 3, the low cycle voltage drive amplitude, VL, 5 is typically a fraction of the high cycle voltage drive amplitude, VH, 6. For a source whose output approximates very closely that of a blackbody, such as a Micro-Electro-Mechanical Source (MEMS), the design objective is to achieve a source blackbody temperature of ~200° C. during the low amplitude drive cycle and a temperature of ~400° C. during the high amplitude drive cycle as shown schematically in FIG. 4. In FIG. 4, curve 7 represents a blackbody temperature of ~200° C. for the source during the low amplitude drive cycle and curve 8 represents a blackbody temperature of ~400° C. for the source during the high amplitude drive cycle. Also shown in FIG. 4 is the spectral location 9 for the designed filter 3 (see FIG. 2) specified above for the current invention, namely with a CWL=4.285µ and a FWHM=0.049µ.

Figure 5:
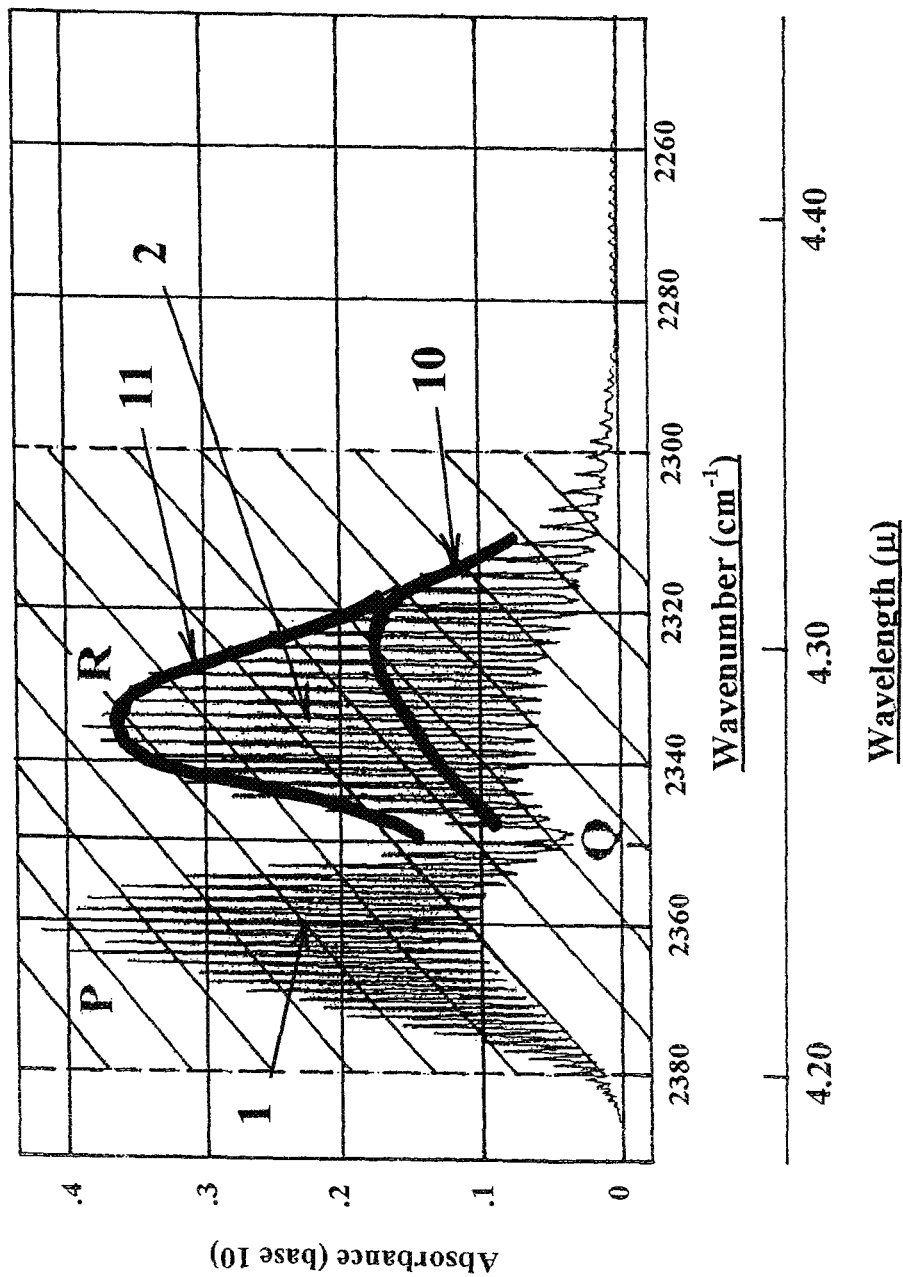
FIG. 5. Convoluted spectral radiation outputs for the source during the low and high amplitude drive cycles.

FIG. 5 shows respectively the convoluted spectral output 10 of the source output 7 and that for the designed spectral filter characteristics 3 (see FIG. 2) during the low amplitude drive cycle when the temperature of the source is ~200° C. FIG. 5 also shows the convoluted spectral output 11 of the source output 8 and that for the designed spectral filter characteristics 3 (see FIG. 2) during the high amplitude drive cycle when the temperature of the source is ~400° C. Also shown in FIG. 5 is the R branch 2 of the CO2 absorption band at 4.259µ. One can see from FIG. 5 that for a particular concentration of CO2 gas in the sample chamber, there is more absorption of the source radiation during the high amplitude drive cycle than that during the low amplitude drive cycle. For the high amplitude drive cycle, the strongest sharp lines of the R branch coincide with the peak of the convoluted spectral radiation output of the source whereas for the low amplitude drive cycle, the strongest sharp lines of the R branch coincide only with the rising portion of the convoluted spectral radiation output. Thus there exists an absorption bias between the Signal channel (high amplitude drive cycle) and the Reference channel (low amplitude drive cycle) for the currently invented Single Beam design methodology similar to that taught in U.S. Pat. No. 8,143,580. The Signal channel (high amplitude drive cycle) is designed to effectively have a longer sample chamber path length than the Reference channel (low amplitude drive cycle) thereby creating the needed absorption bias.

Figure 6:
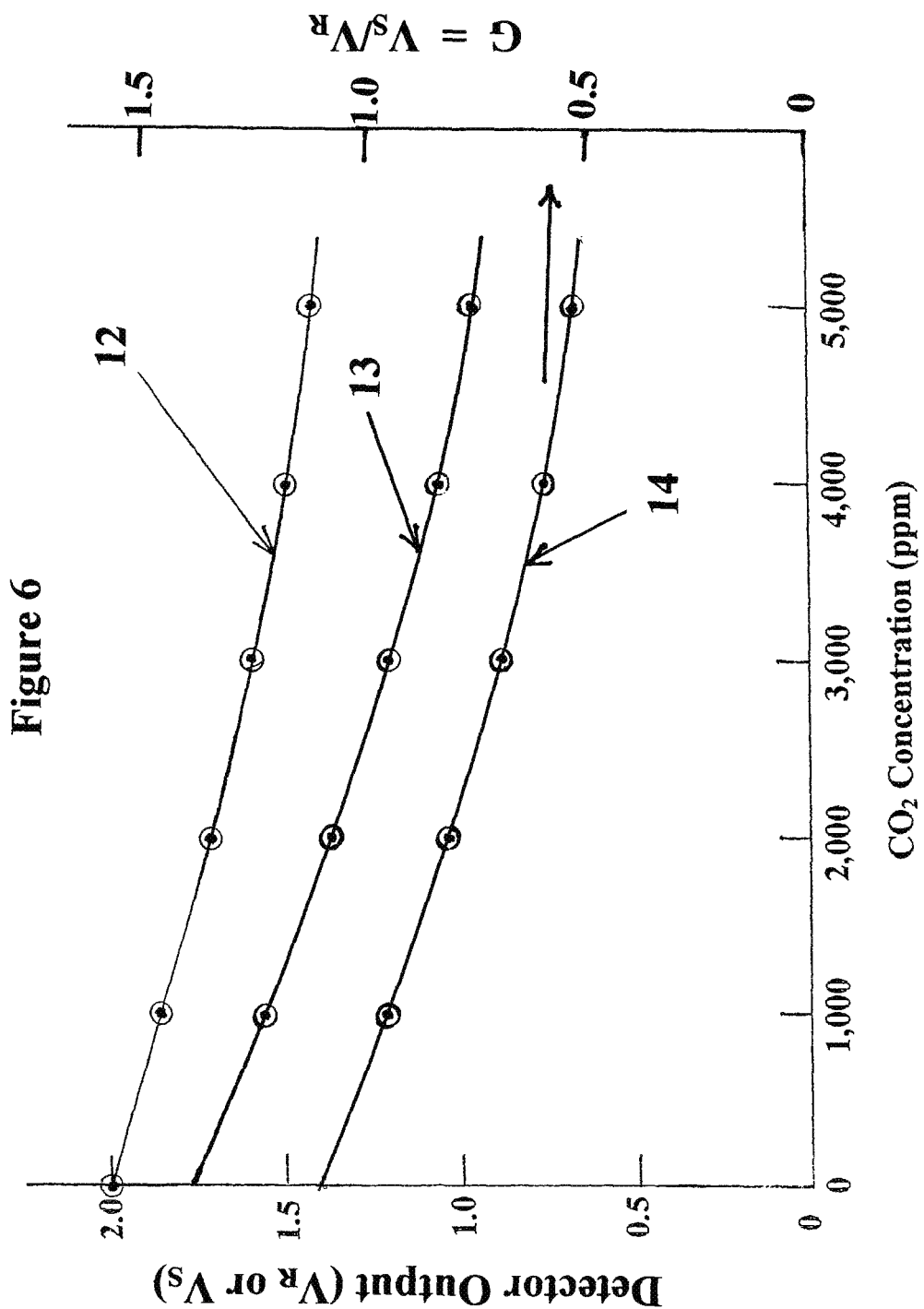
FIG. 6. Signal processing curves for the differential temperature source single beam gas measurement technique.

Curve 12 of FIG. 6 shows the output VR of the Reference channel detector (during the low amplitude drive cycle) as a function of CO2 concentrations in the sample chamber. Curve 13 of FIG. 6 shows the output VS of the Signal channel detector (during the high amplitude drive cycle) as a function of CO2 concentrations in the sample chamber. An NDIR CO2 gas sensor implementing the Absorption Biased methodology processes the value of the ratio G=VS/VR as a function of CO2 concentrations in the sample chamber. Such a functional relationship between the ratio G and the CO2 concentrations in the sample chamber is the de facto calibration curve for the sensor as depicted by Curve 14 of FIG. 6. This de facto calibration curve 14 is further formulated by normalizing the value of G=VS/VR by G0 or X=G/G0 where Go is the value of G=VS/VR when there no target gas, in this case CO2, present in the sample chamber.

Figure 7:
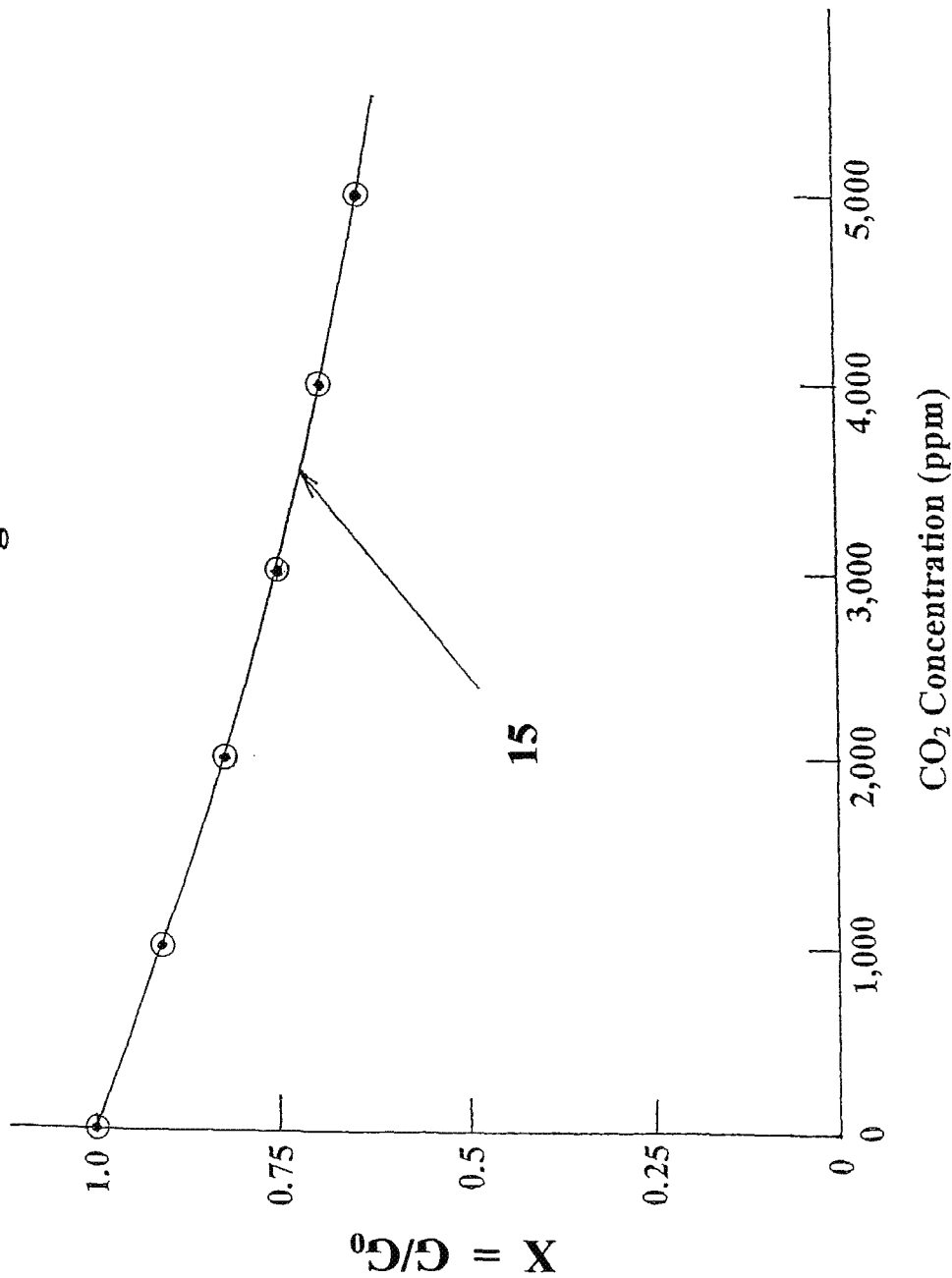
FIG. 7. Calibration curve for the differential temperature source single beam gas measurement technique.

This special formulation of the calibration curve for the presently invented differential temperature source Single Beam gas measurement technique as shown by Curve 15 for the CO2 gas in FIG. 7 follows closely the teaching of U.S. Pat. No. 8,143,580 for an absorption Biased designed NDIR gas sensor. This calibration curve enables us to separate the invariant Physics constituent of the NDIR gas measurement principle from the other inevitably changing components constituent of the sensor over time. In other words, any changes in the calibration curve of the presently invented differential temperature source Single Beam NDIR gas sensor will only be reflected in the changing value of G0 over time. It will not be reflected in the Physics measurement principle for such an NDIR gas sensor which is supposed to always remain invariant.

Figure 8:
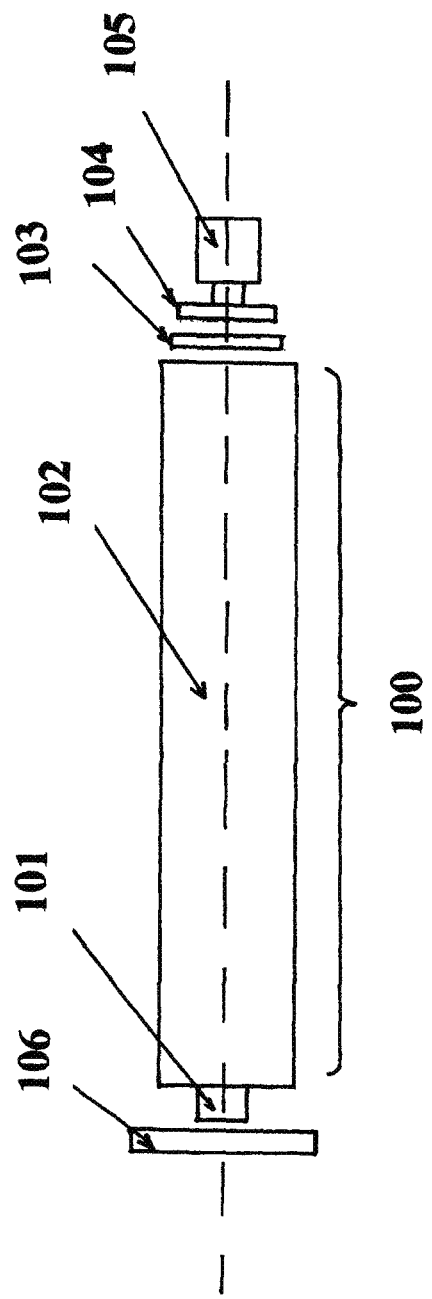
FIG. 8. Block diagram illustrating core elements of a single beam NDIR gas sensor in accordance with the present invention.

FIG. 8 conceptually illustrates a single-beam NDIR gas sensor, shown generally as 100, made in accordance with the teachings set forth above. A single light source 101 is alternatively pulsed between a high temperature and a low temperature by electronics 106 so that it emits radiation into sample chamber 102. A narrow band pass filter 103 with a spectral characteristic that substantially overlaps a strong absorption band for the chosen gas is located between the single infrared source 101 and a detector 104. Detector 104 provides electrical output to electronics 105 for determining a sample concentration of the chosen gas by use of an absorption bias between a signal output of the detector at the high temperature and a reference output of the detector at the low temperature. As discussed above, a convoluted output of the single infrared source 101 and the narrow band pass filter 103 is substantially coincident with the strong absorption band of the gas being detected at the high temperature. Such a sensor can be recalibrated according to the teachings set forth in U.S. Pat. No. 8,178,832, the disclosure of which is specifically incorporated herein by reference, or self-commissioning according to the teachings set forth in U.S. Pat. No. 8,217,355, the disclosure of which is specifically incorporated herein by reference; in either such case, instead of relying upon an absorption bias created by a signal channel and a reference channel, the absorption bias is created according to the teachings set forth herein, and either recalibration or auto-calibration is achieved in the same manner as taught in such references.

Thus, while the invention has been described herein with reference to certain embodiments, those embodiments have been presented by way of example only, and not to limit the scope of the invention. Additional embodiments thereof will be obvious to those skilled in the art having the benefit of this detailed description. Further modifications are also possible in alternative embodiments without departing from the inventive concept as defined by the following claims.

What is claimed is:

1. A process for determining a sample concentration of a chosen gas in a single beam Non-Dispersive Infrared ("NDIR") gas sensor, comprising:
   emitting infrared radiation from a single infrared source into a sample chamber that is alternatively pulsed at a high temperature and at a low temperature;
   detecting infrared radiation that is alternatively pulsed at the high temperature and at the low temperature by a detector after it passes through a narrow band pass filter with a spectral characteristic that substantially overlaps a strong absorption band for the chosen gas; and
   determining the sample concentration of the chosen gas by use of an absorption bias between a signal output of the detector at the high temperature and a reference output of the detector at the low temperature;
   wherein a convoluted output of the single infrared source and the narrow band pass filter is substantially coincident with the strong absorption band.

2. A single beam Non-Dispersive Infrared ("NDIR") gas sensor for detecting the presence of a chosen gas, comprising:
   a single infrared source for generating infrared radiation into a sample chamber that is alternatively pulsed between a high temperature and a low temperature;
   a detector located in the sample chamber;
   a narrow band pass filter with a spectral characteristic that substantially overlaps a strong absorption band for the chosen gas located between the single infrared source and the detector; and
   electronics for determining a sample concentration of the chosen gas by use of an absorption bias between a signal output of the detector at the high temperature and a reference output of the detector at the low temperature;
   wherein a convoluted output of the single infrared source and the narrow band pass filter is substantially coincident with the strong absorption band at the high temperature.

* * * * *